United States Patent [19]

Sury et al.

[11] 4,066,642
[45] Jan. 3, 1978

[54] PROCESS FOR THE PRODUCTION OF THIOPHOSPHORIC ACID ESTERS

[75] Inventors: Yel S. Sury, Baton Rouge, La.; James M. Lignos, East Mobile, Ala.

[73] Assignee: Ciba-Geigy Corporation, Ardsley, N.Y.

[21] Appl. No.: 678,326

[22] Filed: Apr. 19, 1976

Related U.S. Application Data

[63] Continuation-in-part of Ser. No. 411,992, Nov. 1, 1973, abandoned.

[51] Int. Cl.$^2$ .............................................. C07F 9/65
[52] U.S. Cl. .............................................. 260/251 P
[58] Field of Search ........................... 260/251 P, 973

[56] References Cited

U.S. PATENT DOCUMENTS

| 2,754,243 | 7/1956  | Gysin et al. ............ 260/251 P X |
| 3,004,054 | 10/1961 | Smithey, Jr. ............ 260/973 |
| 3,107,246 | 10/1963 | Ferguson ................ 260/251 |
| 3,329,678 | 7/1967  | Curry et al. ............ 260/251 |
| 3,432,503 | 11/1969 | Ferguson ................ 260/251 P |
| 3,741,968 | 6/1973  | Haubein ................. 260/251 P |

Primary Examiner—Donald G. Daus
Assistant Examiner—DianaG. Rivers
Attorney, Agent, or Firm—Karl F. Jorda

[57] ABSTRACT

An improved process for the production of dialkoxy phosphoric acid esters of substituted hydroxypyrimidines which involves reacting a dialkyl phosphoric acid halide with a substituted hydroxypyrimidine at elevated temperatures and in the presence of an inert non-polar organic solvent and an acid binding agent but without catalyst, wherein the phosphoric acid halide and sodium or potassium hydroxide in molar excess of about 5 to 10% are added to a reaction mixture in reflux consisting essentially of the hydroxypyrimidine in molar excess of about 1 to 5% and the non-polar solvent at uniform rates over a period of 1 to 7 hours while removing water substantially as it is formed thereby impeding formation of cholinesterase inhibiting impurities. A preferred embodiment is the preparation of Diazinon.

3 Claims, No Drawings

PROCESS FOR THE PRODUCTION OF THIOPHOSPHORIC ACID ESTERS

CROSS-REFERENCE TO RELATED APPLICATIONS

This application is a continuation-in-part of application, Ser. No. 411,992, filed Nov. 1, 1973, now abandoned.

DETAILED DISCLOSURE

This invention relates to an improved process of preparing esters of thiophosphoric acid and, more specifically, thiophosphoric acid esters of substituted hydroxypyrimidines.

More particularly, the present invention pertains to the manufacture of esters of dialkoxy thiophosphoric acids of the following general formula:

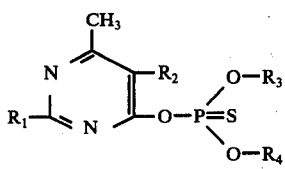

I wherein $R_1$ represents lower alkyl, lower alkenyl, lower alkoxy(lower)alkyl or lower alkylmercapto(lower)alkyl, $R_2$ stands for hydrogen, lower alkyl or lower alkenyl and $R_3$ and $R_4$ are lower alkyl.

These compounds which are disclosed and claimed in U.S. Pat. No. 2,754,243, and especially O,O-diethyl-O-(2-isopropyl-4-methyl-6-pyrimidyl) thiophosphate (Diazinon), are of great commercial value by virtue of their well-established insecticidal and acaricidal activity and consequent usefulness in pest control.

According to prior art practices, the compounds of the above formula were initially produced by reacting an aliphatic thiophosphoric acid diester halide of the formula:

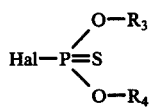

II wherein Hal represents chlorine or bromine and $R_3$ and $R_4$ are as defined hereinabove, with a hydroxypyrimidine of the formula:

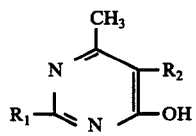

III wherein $R_1$ and $R_2$ have the significance given to them above, in the presence of benzene as solvent and an alkali metal carbonate as acid binding agent.

However, the practice of such a process entailed certain drawbacks and disadvantages. Thus, for example, it was not possible to use as acid binding agent, in lieu of potash, soda ash which is appreciably less expensive, i.e., only 15-25% of the cost of potash, inasmuch as with soda ash yields of less than 20% are obtainable even if the reaction time is in excess of 24 hours. But even with potash being used, the total reaction time was too long from the point of view of commercial feasibility, e.g., in excess of 16 hours.

It was then found that dialkoxy thiophosphates of Formula I could be advantageously produced in a considerable shortened period of time by means of a procedure which utilized various catalysts, as for instance, mercury salts, e.g. mercury chlorides and iodides (U.S. Pat. No. 3,107,245) and copper salts, e.g. cupric chloride and cupric nitrate (U.S. Pat. Nos. 3,107,246 and 3,367,935), especially when added to the reaction mixture during the course of refluxing as small aliquots of a solution of the catalyst (U.S. Pat. No. 3,329,678).

However, while these catalytic processes constituted advancements and improvements in the production of the subject dialkoxy thiophosphates, other problems and disadvantages surfaced. It was found that in these processes, e.g., in the conventional and commercial sodium carbonate/copper chloride process, significant amounts of impurities were frequently produced which increase the cholinesterase activity of these phosphoric acid esters. The presence of a catalyst contributes to the formation of cholinesterase-inhibiting impurities by catalyzing side reactions. These impurities are in the production of Diazinon, for example, S-TEPP (monothionotetraethylpyrophosphate), SS-TEPP (dithionotetraethylpyrophosphate), the oxo-derivative (which has oxygen in lieu of the sulfur atom) and others the exact nature of which is not known. These impurities are formed in amounts of 0.5% or greater. Significant amounts of such cholinesterase-inhibiting impurities are also formed after manufacture due to decomposition of these phosphoric acid esters.

The term "cholinesterase activity" as used herein means inhibition of the enzymatic activity of cholinesterase. This inhibition interferes with the hydrolysis of acetylcholine and allows the accumulation of sufficiently large amounts of acetylcholine to affect nerve activity and corresponding muscular control adversely. [Wayland J. Hays, Chemical Handbook on Economic Poisons, U.S. Dept. of Health, Education and Welfare, p. 12 (1963)].

An increase of the cholinesterase activity of the subject phosphoric acid esters due to cholinesterase-inhibiting impurities is undesirable from the point of view of operators who handle these phosphoric acid esters or warm blooded animals that may come into contact therewith. Accordingly, when in the past a batch of phosphoric acid esters either by formation during manufacture or by decomposition after manufacture contained those undesirable chlorinesterase-inhibiting impurities to the extent of less than 1 gamma, the batch could not be utilized commercially and was destroyed.

In present commercial practice these chlorinesterase-inhibiting impurities had to be removed in a separate subsequent processing step involving the refluxing of the reaction product in an inert organic solvent with a basic material such as sodium hydroxide. See U.S. Pat. No. 3,432,503.

It is the principal object of this invention to produce dialkoxy thiophosphates of formula I of excellent quality and color and in excellent yield.

It is a further important object of this invention to minimize and reduce the formation of these undesirable chlorinesterase-inhibiting impurities during the reaction so that the desired product contains at most only trace amounts and so that no separate removal operation is necessary.

The above-mentioned objectives can be accomplished by the process of this invention which comprises condensing a thiophosphoric acid diester halide of formula II and a hydroxypyrimidine of formula III — without any catalyst present — at an elevated temperature in a non-polar solvent and with sodium or potassium hydroxide as acid acceptor and with careful control of the mode of addition of the reactants.

More particularly, the process according to the invention involves refluxing an inert non-polar organic solvent, e.g., benzene, toluene, cyclohexane, dichloroethane, trichloroethane, a mixture of n-heptane and trichloroethane, etc., and a hydroxypyrimidine of formula III, followed by concomitant addition at uniform rates over 1 to 7 hours of a thiophosphoric acid diester halide of formula II and of 50% sodium or potassium hydroxide solution. The reactant of formula III is employed as a 1–5% molar excess and the acid binding agent is added as a 5–10% molar excess over reactant II.

The CHI value of the material made, e.g., by using copper catalyst is known to vary from 1.8 (toxic) to 2 gamma (the impurities SS-TEPP, S-TEPP and oxo-Diazinon are in amounts of 0.5% or greater); while the CHI value of the material with the new invention is always greater than 3.6 gamma (CHI impurities being less than 0.5%). Cf. U.S. Pat. No. 3,432,503 for the meaning and determination of CHI values.

It is surprising in view of the prior art practices which utilize weak bases as acid binding agents in the belief that strong bases in large concentrations would decompose the thiophosphoric acid diester chloride or the final product, that a strong base not only can be employed but this can be done to great advantage, provided careful control during the addition of the reactants to the reaction mixture is exercised so as to favor formation of the desired esters, and water which is formed during the reaction is removed quickly.

To avoid hydrolysis of said diester chloride or the final product, water of dilution must be removed substantially as it is formed. An adequate rate or removal of water for a one-gram-mole laboratory batch was found to be 0.4–0.5 ml/min.

Apart from the use of a cheaper materials as acid binding agent, other important advantages can be realized according to the present inventive concept, as for instance:

1. the average reaction time of the subject process is only 6–7 hours;

2. the non-polar solvents employed, apart from being less expensive, facilitate product and solvent recovery without extensive purification and recovery systems because they are immiscible with water;

3. no toxic metal catalyst need be used which eliminates the corresponding effluent problem and the product is substantially free of chlorinesterase-inhibiting impurities;

4. since no copper catalyst is used and the product is substantially free of chlorinesterase-inhibiting impurities, caustic treatment for purification as e.g. disclosed in U.S. Pat. No. 3,432,503 is unnecessary;

5. to remove the excess hydroxypyrimidine a single caustic wash without refluxing followed by a water wash (pH 8–9) is sufficient in the subject process to ensure good quality product;

6. a filtration step to remove solid material (soda ash and copper catalyst) is not necessary in the subject process; a single Sparkler type filtration following the wash cycle is sufficient.

The invention may be illustrated, without limitation thereto, by the following example.

EXAMPLE 1

In a 2-liter, 5-neck flask equipped with thermometer, blade stirrer, two dropping funnels, provided with rotameters for control of reactant addition, electric heating mantle, Barret distillate receiver and Friedrich condenser, a mixture of 275 g of benzene and 160 g 2-isopropyl-4-methyl-6-hydroxypyrimidine, hereinafter "oxypyrimidine", 100% (1.05 moles, 5% excess based on diethyl thiophosphoric acid chloride, hereinafter, "ester chloride") is heated to reflux (83° C), whereupon 188.5 g ester chloride 100% (1.0 moles) and 88 g of 50% sodium hydroxide (1.1 moles, 10% excess based on ester chloride) are started in dropwise. The ester chloride is added in 1½–2 hours (the ester chloride addition should be completed 15–30 minutes before completion of the sodium hydroxide addition). The addition of ester chloride is done at a constant rate. The temperature is increased as rapidly as possible without causing boil-over (~7° per hour) and the water is collected in the receiver. (NOTE: The rate of water removal should be 0.4–0.5 ml/min during the ester chloride/sodium hydroxide addition.) The reaction is completed when the ester chloride level is less than 0.25% by glc analysis (6–7 hours from start of ester chloride and sodium hydroxide additions.) After the reaction is completed, the reaction mass is cooled to 60°–70° C and 400 g of water solution is added as a wash and agitated for 15 minutes at 50°–60° C. After phase separation, 400g of water and 120 g of 50% of sodium hydroxide is added and the pH is adjusted to 8.0–9.0 with 5% sulfuric acid. After separation the Diazinon/benzene layer is vacuum filtered (filter should be precoated with Solka floc) then stripped to 105° on the toto-vac at 25–30 in. Hg. A yield of 94–95% based on ester chloride charged is obtained (yield based on GC assay).

Additional runs following the procedure of Example 1 are illustrated in the following table.

TABLE

| | Charges (Moles) | | | Addition Time (Hours) | | | Rate of Water Removal ml/min | React. Time (Hours) | Ester Chloride unreacted (Wt.%) | Wt. Tech Diazinon | Rate of NaOH Addition | Rate of Ester Chloride Addition |
|---|---|---|---|---|---|---|---|---|---|---|---|---|
| | Ester Chloride | Oxypyrimidine | NaOH | Benzene | Ester Chloride | NaOH | | | | | | |
| 1) | 1.00 | 1.05 | 1.10 | 2.7 | 1.7 | 1.6 | 0.4 | 4.0 | 0.6 | 281.6 | 0.9g/min | 1.8g/min |
| 2) | 1.00 | 1.05 | 1.10 | 2.7 | 1.8 | 2.0 | 0.4 | 5.5 | 0.1 | 281.3 | 0.7g/min | 1.7g/min |
| 3) | 1.00 | 1.10 | 1.15 | 2.7 | 2.1 | 3.7 | 0.3 | 4.5 | 0.2 | 285.8 | 0.4g/min | 1.5g/min |
| 4) | 1.00 | 1.05 | 1.10 | 2.7 | 2.5 | 2.0 | 0.3 | 5.5 | 0.2 | 287.0 | 0.7g/min | 1.3g/min |
| 5) | 1.00 | 1.05 | 1.10 | 2.7 | 2.6 | 2.6 | 0.1 | 5.0 | 0.1 | 292.0 | 0.6g/min | 1.2g/min |
| 6) | 1.00 | 1.05 | 1.10 | 2.7 | 1.0 | 2.2 | 0.5 | 5.0 | 0.2 | 289.0 | 0.7g/min | 3.1g/min |
| 7) | 1.00 | 1.05 | 1.10 | 2.7 | 2.2 | 2.2 | 0.4 | 5.0 | 0.2 | 291.3 | 0.7g/min | 1.4g/min |
| 8) | 1.00 | 1.05 | 1.10 | 2.7 | 1.6 | 1.7 | 0.5 | 4.0 | 0.2 | 294.1 | 0.9g/min | 2.0g/min |
| 9) | 1.00 | 1.05 | 1.10 | 2.7 | 2.0 | 2.3 | 0.5 | 5.0 | 0.1 | 295.5 | 0.6g/min | 1.6g/min |

TABLE-continued

| | Color Gardner | Benzene | Ester Chloride | Oxypyrimidine | SS-TEPP | S-TEPP | Oxo-DIAZINON | CHI | Yield or Assay | Yield Based on Ester Chloride Charged and GC Assay |
|---|---|---|---|---|---|---|---|---|---|---|
| 1) | 7 | 1.0 | 0.2 | 0.1 | Tr | ND | ND | 3.6 | 96.6 | 90.2 |
| 2) | 10 | 0.6 | 0.1 | Tr | Tr | ND | ND | 3.6 | 98.3 | 94.1 |
| 3) | 11 | 1.0 | 0.2 | 0.1 | 0.2 | ND | ND | 3.6 | 96.6 | 92.5 |
| 4) | 11 | — | 0.4 | 0.4 | 0.1 | ND | ND | 3.6 | 96.5 | 91.1 |
| 5) | 11 | 0.8 | 0.3 | 0.5 | Tr | ND | ND | 3.6 | 96.0 | 92.1 |
| 6) | 8 | 0.5 | 0.2 | 0.2 | Tr | ND | ND | 3.6 | 96.9 | 92.1 |
| 7) | 11 | 0.4 | 0.2 | 0.1 | Tr | ND | ND | 3.6 | 98.0 | 93.9 |
| 8) | 11 | 0.3 | 0.3 | 0.1 | Tr | ND | ND | 3.6 | 98.0 | 94.8 |
| 9) | 11 | 0.5 | 0.2 | 0.1 | Tr | ND | ND | 3.6 | 97.7 | 94.8 |

What is claimed is:

1. In a process for the production of thiophosphoric acid esters of the formula I

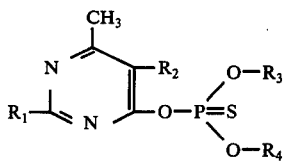

wherein $R_1$ is lower alkyl, lower alkenyl, lower alkoxy(lower)alkyl or lower alkylmercapto(lower)alkyl, $R_2$ is hydrogen, lower alkyl or lower alkenyl and $R_3$ and $R_4$ are lower alkyl, which comprises reacting a dialkyl phosphoric acid halide of the formula II

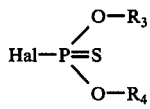

wherein Hal represents chlorine or bromine and $R_3$ and $R_4$ are as defined hereinabove, with a hydroxypyrimidine of the formula III

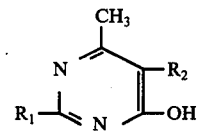

wherein $R_1$ and $R_2$ have the significance given to them above, at elevated temperatures and in the presence of an organic solvent and an acid binding agent, the improvement which comprises adding the reactant of formula II and sodium or potassium hydroxide concomitantly to a reaction mixture in reflux consisting essentially of reactant of formula III and an inert non-polar organic solvent at uniform rates over a period of 1 to 7 hours while removing water substantially as it is formed, said reactant of formula III being in a molar excess of about 1 to 5% and said acid binding agent being in a molar excess of about 5 to 10%, and said reaction being carried out in the absence of a catalyst.

2. A process as claimed in claim 1, wherein the solvent is dichloroethane or trichloroethane.

3. A process as claimed in claim 1, wherein the reactant of formula II is o,o-diethyl thiophosphoric acid chloride and the reactant of formula III is 2-isopropyl-4-methyl-6-hydroxypyrimidine.

* * * * *